United States Patent [19]

Takagi

[11] 4,361,139
[45] Nov. 30, 1982

[54] SCIRROSCOPE

[75] Inventor: Takeji Takagi, Machida, Japan

[73] Assignee: Olympus Optical Company Ltd., Japan

[21] Appl. No.: 174,236

[22] Filed: Jul. 31, 1980

[30] Foreign Application Priority Data

Nov. 20, 1979 [JP] Japan .................................. 54-150521

[51] Int. Cl.³ .............................................. A61B 1/06
[52] U.S. Cl. ........................................................ 128/6
[58] Field of Search ................................. 128/6, 3–5, 128/7–9, 303.15, 634, 665; 350/96.26; 356/241

[56] References Cited

U.S. PATENT DOCUMENTS 3,091,235  5/1963  Richards .................................. 128/6
3,434,775  3/1969  Gosselin .................................. 128/6
3,776,222  12/1973  Smiddy .................................. 128/6

FOREIGN PATENT DOCUMENTS 2805451  8/1978  Fed. Rep. of Germany .......... 128/6

Primary Examiner—Gene Mancene
Assistant Examiner—Mickey Yu
Attorney, Agent, or Firm—Ostrolenk, Faber, Gerb & Soffen

[57] ABSTRACT

A scirroscope includes a pipe-shaped shell tube, a channel for feeding water or passing a treatment instrument therethrough, an optics tube in which an observation optical system is disposed, and a bundle of optical fibres which defines an illumination optical system. An elastic member covers at least partly at least one of the internal periphery of the shell tube and the external periphery of the channel, the optics tube and the fibre bundle.

9 Claims, 7 Drawing Figures

SCIRROSCOPE

BACKGROUND OF THE INVENTION

The present invention relates to a scirroscope, namely, an endoscope having a rigid and straight sheath or shell tube, in particular, to scirroscope which is shock resistant.

A drawback of known scirroscopes is that they are susceptible to shocks because of the principal materials, such as metal or glass, which are used to form them. In particular, if a scirroscope is dropped inadvertently during use, it is likely that the shock will cause a misalignment of the optical system or water leakage. A scirroscope includes pipes and other members which are directly joined to each other by adhesives. These members exhibit different coefficients of thermal expansion, which may give rise to an exfoliation if the scirroscope is sterilized under heat or cleaned with hot water.

FIG. 1 illustrates an example of a conventional scirroscope 1, including a portion 2A adapted to be inserted into a coeliac cavity and an operating end 2B. The portion 2A comprises a shell tube 3 formed of a metal and configured as a pipe in which are disposed a channel 4 for feeding water or passing a treatment instrument or the like, and an optical tube 6 having an observation optical system 5 disposed therein as well as an illumination optical system 8, formed by a bundle of optical fibres 7. The observation system 5 includes a protecting glass 9 attached to its distal end, and a plurality of lenses 10 disposed therein which are used to convey an image being observed. The operating end 2B comprises an observation eyepiece assembly 11, a fixture 12 for an illumination light guide, and a fitting 13 for connection with a hose which is used to feed water into the channel 4 and having a feedwater control cock 14 associated therewith.

Parts of the portion 2A are formed of metal, glass, glass fibre and the like materials which are susceptible to damage by shocks. Additionally, these parts are directly joined to each other by adhesives, and this causes any externally applied shock to be directly transmitted to objects located within them, with the result that the optical axis of the optical system may be misaligned and the lenses broken. Also, a relative displacement between the parts as well as cracks in them are caused by different coefficients of thermal expansion thereof.

SUMMARY OF THE INVENTION

It is an object of the invention to eliminate the above disadvantages, by providing a scirroscope in which the internal or external periphery of the shell tube, channel, optics tube and bundle of optical fibres which form the portion adapted to be inserted into a coeliac cavity is provided with a coating of a tubular elastic material such as rubber or plastic.

In accordance with the invention, the provision of a coating of an elastic material such as rubber or plastic on the internal or external periphery of a shell tube, optics tube, channel and optical fibre bundle which form a portion of a scirroscope adapted to be inserted into a coeliac cavity and which are by materials such as glass, metal and glass fibre is effective to attenuate any external shock, which may be produced as a result of drop during use, as it is transmitted to an inner part or parts, thus avoiding a misalignment of the optical system or breakage of lenses. The elastic material such as rubber or plastics exhibits a lower thermal conductivity, minimizing the conduction of heat to the interior if heat is applied to the scirroscope when sterilizing it in an autoclave or other equipment. The resilience of the elastic material accommodate for some differences in the coefficient of thermal expansion among the parts, thus acting as a buffering element therebetween to eliminate the occurrence of an exfoliation or cracks.

DESCRIPTION OF PREFERRED EMBODIMENTS

Figure 1:
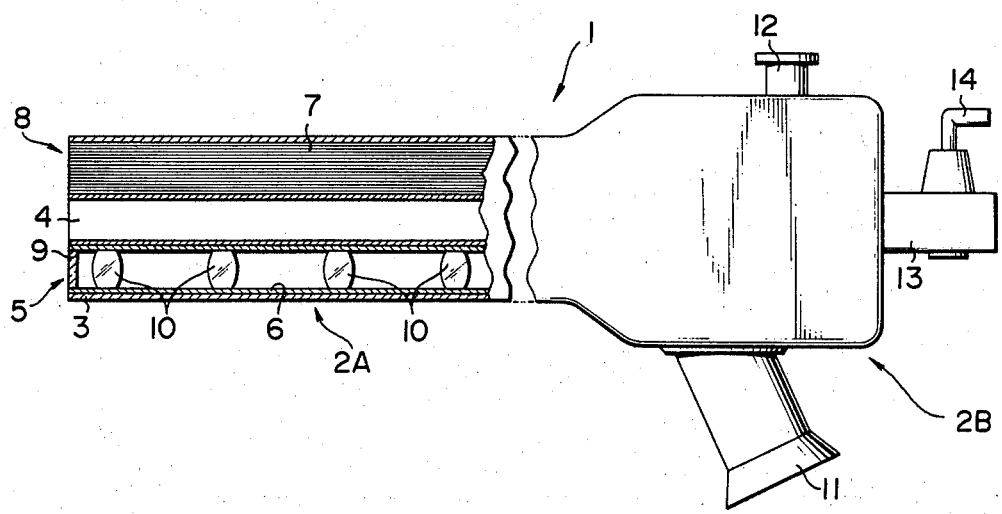
FIG. 1 is a side elevation of an example of a conventional scirroscope, with a portion to be inserted into a coeliac cavity shown in section.
Figure 2A:
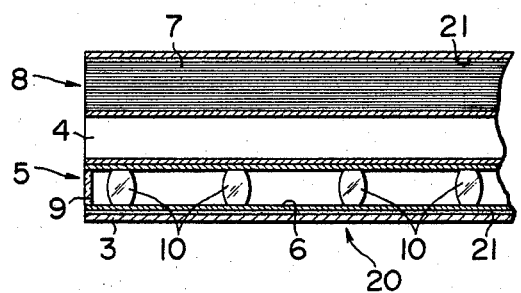
FIGS. 2 to 4 (a) and (b) are axial and transverse sections of several embodiments of the invention, respectively.

FIGS. 2(a) and (b) are sections of essential parts of a portion 20 of a scirroscope according to one embodiment of the invention which is adapted to be inserted into a coeliac cavity. Corresponding parts to those shown in FIG. 1 are designated by like reference characters, and hence will not be described.

An elastic member 21 is integrally bonded, as by adhesive or crimping, to the internal periphery of the shell tube 3 of the portion 20, and an adhesive is applied to the interface between the internal periphery of the elastic member and another member which contacts it, such as the optics tube 6 and the fibre bundle 7. In this manner, such inner member is integrally bonded to the elastic member 21 as by adhesion or crimping.

The presence of the elastic member 21, which absorbs some of the shock applied to the shell tube 3 (as might be produced as the latter is dropped) minimizes the influence of the shock upon internal parts, thus minimizing the likelihood that the optical system 5 may be damaged. The reduced thermal conductivity of the elastic member 21, formed by rubber, plastic or the like, retards the heat transfer to the interior, whereby a temperature difference which causes an exfoliation or cracks is advantageously reduced.

Figure 2B:
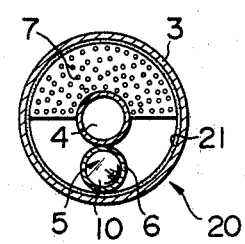
Figure 3A:
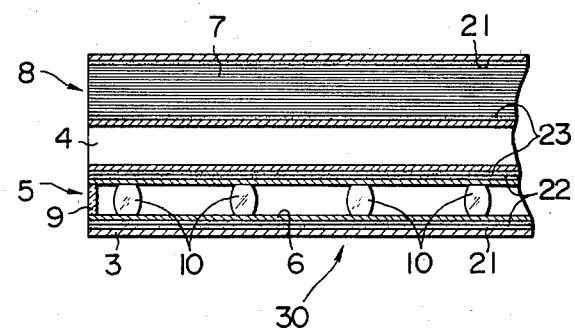

FIGS. 3(a) and (b) show another embodiment of the invention where a portion 30 of scirroscope shown is provided with a coating in the form of an elastic member applied to the inner periphery of the shell tube 3, in the same manner as shown in FIG. 2. Additionally, it is provided with elastic members 22 and 23 on the outer periphery of the optics tube 6 and the channel 4, respectively. Other parts correspond to those shown in FIGS. 1 and 2.

Since the portion 30 is provided with elastic members 21, 22, 23, formed of rubber, plastic or the like, which coat the internal periphery of the shell tube 3 and the external periphery of the optics tube 6 and the channel 4, the portion 30 exhibits a heat and a shock resistance which are comparable to or even exceed those of the portion 20 shown in FIG. 2.

Figure 3B:
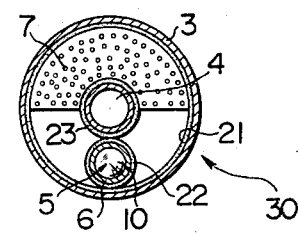
Figure 4A:
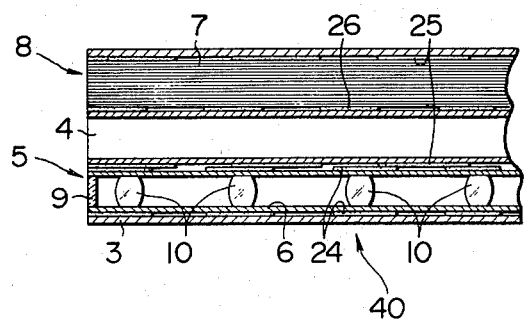

FIGS. 4(a) and (b) show a further embodiment of the invention where a portion 40 of a scirroscope which is adapted to be inserted into a coeliac cavity is provided with a plurality of ring-shaped elastic members 24 coating the external periphery of the optics tube 6, a plurality of tubular elastic members 25 of a reduced length coating the external periphery of both the fibre bundle 7 and the channel 4, and an elastic member 26 in a trapezoidal form and having a reduced length covering onehalf the external periphery of the channel 4. Again, corresponding parts to those shown in FIGS. 2 and 3 are designated by like reference characters and will not be described.

Figure 4B:
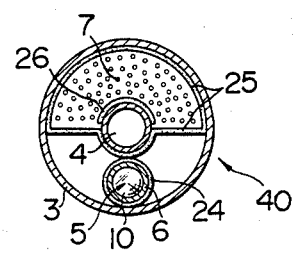

The use of pluralities of elastic members 24, 25, 26, though of reduced lengths, to cover various parts in the embodiment of FIG. 4 is also effective to absorb shocks applied, preventing the occurrence of an exfoliation or cracks under heat.

What is claimed is:

1. A scirroscope comprising:
   (A) a rigid, non-flexible outer tubing;
   (B) a plurality of articles housed in said tubing, said articles including an observation optical system and an illumination optical system;
   (C) an elastic, resilient, shock absorbing member covering at least one of:
      (1) the internal periphery of said rigid outer tubing; and
      (2) the outer periphery of one of said articles;
   (D) said member serving to attenuate and absorb external shock and vibrations transmitted through said rigid outer tubing so that at least one of said articles is mechanically insulated from external mechanical shock and vibrations applied to said rigid outer tubing, said member also serving as a buffer that permits differences in thermal expansion of components of said scirroscope to occur without producing damage to said scirroscope.

2. A scirroscope according to claim 1, wherein said observation optical system comprises an optical tube having a plurality of lenses housed therein, said illumination optical system comprises a bundle of optical fibres and said articles further include a channel which may be used to feed liquid or pass a treatment instrument.

3. A scirroscope according to claim 1, wherein said elastic member at least partially coats said one of said articles.

4. A scirroscope according to claim 1, wherein said elastic member is formed of rubber or plastic.

5. A scirroscope according to claim 1, wherein said elastic member is a first elastic member and covers said outer periphery of one of said articles and wherein said scirroscope further includes a second elastic member covering the outer periphery of a different one of said articles.

6. A scirroscope according to claim 2, wherein said elastic member is a first elastic member and covers the outer periphery of one of said articles and wherein said scirroscope further includes a second elastic member covering the outer periphery of a different one of said articles.

7. A scirroscope according to claim 6, wherein said first elastic member covers the outer periphery of said optical tube and said second elastic member covers the outer periphery of said bundle of optical fibres.

8. A scirroscope according to claim 7, further including a third elastic member covering at least a portion of the outer periphery of said channel.

9. A scirroscope according to claim 1, wherein said elastic member acts as a thermal insulator.

* * * * *